US00PP16632P2

(12) United States Plant Patent
Olesen

(10) Patent No.: US PP16,632 P2
(45) Date of Patent: Jun. 13, 2006

(54) ROSE PLANT NAMED 'POULCOT008'

(50) Latin Name: ***Rosa* hybrid**
Varietal Denomination: Poulcot008

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 101 days.

(21) Appl. No.: 11/002,742

(22) Filed: Dec. 1, 2004

(51) Int. Cl.
*A01H 5/00* (2006.01)

(52) U.S. Cl. ..... Plt./103

(58) Field of Classification Search ..... Plt./103, Plt./144, 107
See application file for complete search history.

*Primary Examiner*—Anne Marie Grunberg
*Assistant Examiner*—June Hwu

(57) ABSTRACT

A new garden rose plant of the shrub rose class which has abundant, white flowers, attractive foliage, and abundant rose hips. This new and distinct variety has shown to be uniform and stable in the resulting generations from asexual propagation.

2 Drawing Sheets

Botanical classification: *Rosa* hybrid.
Variety denomination: 'Poulcot008'.

SUMMARY OF THE INVENTION

The present invention constitute a new and distinct variety of garden rose plant that originated from a controlled crossing between the female seed parent 'Pouldiram', a rose variety by the same inventors, described and illustrated in U.S. Plant Pat. No. 12,568 issued Apr. 23, 2002, and the male pollen parent, an unnamed seedling.

The two parents were crossed during the summer of 1996, and the resulting seeds were planted in a controlled environment in Fredensborg, Denmark. The new variety is named 'Poulcot008'.

The new variety may be distinguished from its female seed parent by the following combination of characteristics:

1. 'Pouldiram' has more flower petals than 'Poulcot008'.
2. 'Pouldiram' has a taller growth characteristic than 'Poulcot008'.

The new variety may be distinguished from its male pollen parent by the following combination of characteristics:

1. The male parent has light pink flowers, while 'Poulcot008' has white flowers.
2. The male parent has a more petals than 'Poulcot008'.

The objective of the hybridization of this rose variety was to create a new and distinct variety for garden use with unique qualities, such as:

1. Uniform and abundant white flowers;
2. Vigorous, but compact growth when propagated both as a budded rose and on its own roots;
3. Exceptional disease resistance;
4. Abundant rose hips.

This combination of qualities is not present in previously available commercial cultivars of this type, known to the inventor, and distinguish 'Poulcot008' from all other varieties of which we are aware.

As part of the rose development program, Mogens N. Olesen germinated the seeds from the aforementioned hybridization during winter of 1996 and conducted evaluations on the resulting seedlings in a controlled environment in Fredensborg, Denmark.

'Poulcot008' was selected in the spring of 1997 by the inventor as a single plant from the progeny of the aforementioned hybridization.

Asexual reproduction of 'Poulcot008' by traditional budding and rooted cuttings was first done by Mogens N. Olesen in the nursery in Fredensborg, Denmark in July 1997. This initial and other subsequent asexual propagations conducted in controlled environments have demonstrated that the characteristics of 'Poulcot008' are true to type and are transmitted from one generation to the next.

BRIEF DESCRIPTION OF THE DRAWING

The accompanying color illustrations show as true as is reasonably possible to obtain in color photographs of this type, the typical characteristics of the buds, flowers, leaves, stems, and seeds of 'Poulcot008'. Specifically illustrated in the drawings:

FIG. 1.2; Flower buds at various stages of development;

FIG. 1.3; Flower petals detached;

FIG. 1.4; Sepals, receptacle, and peduncle;

FIG. 1.5; Mature and juvenile foliage;

FIG. 1.6; Juvenile and mature stem showing thorns;

DETAILED DESCRIPTION OF THE VARIETY

Figure 1:
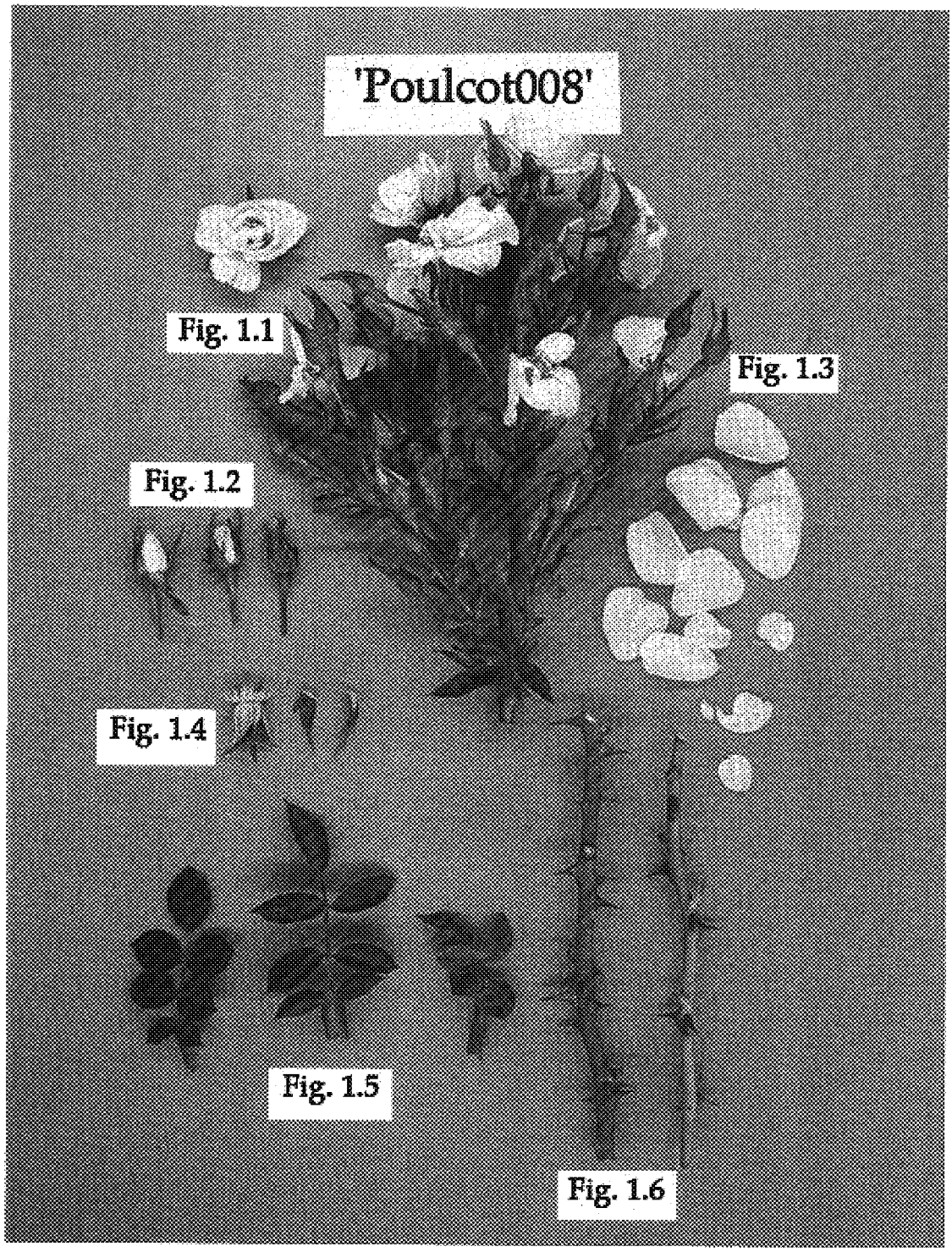
FIG. 1.1; Open flower and flower cluster showing attachment of leaves, pedicels, and flower buds.
Figure 2:
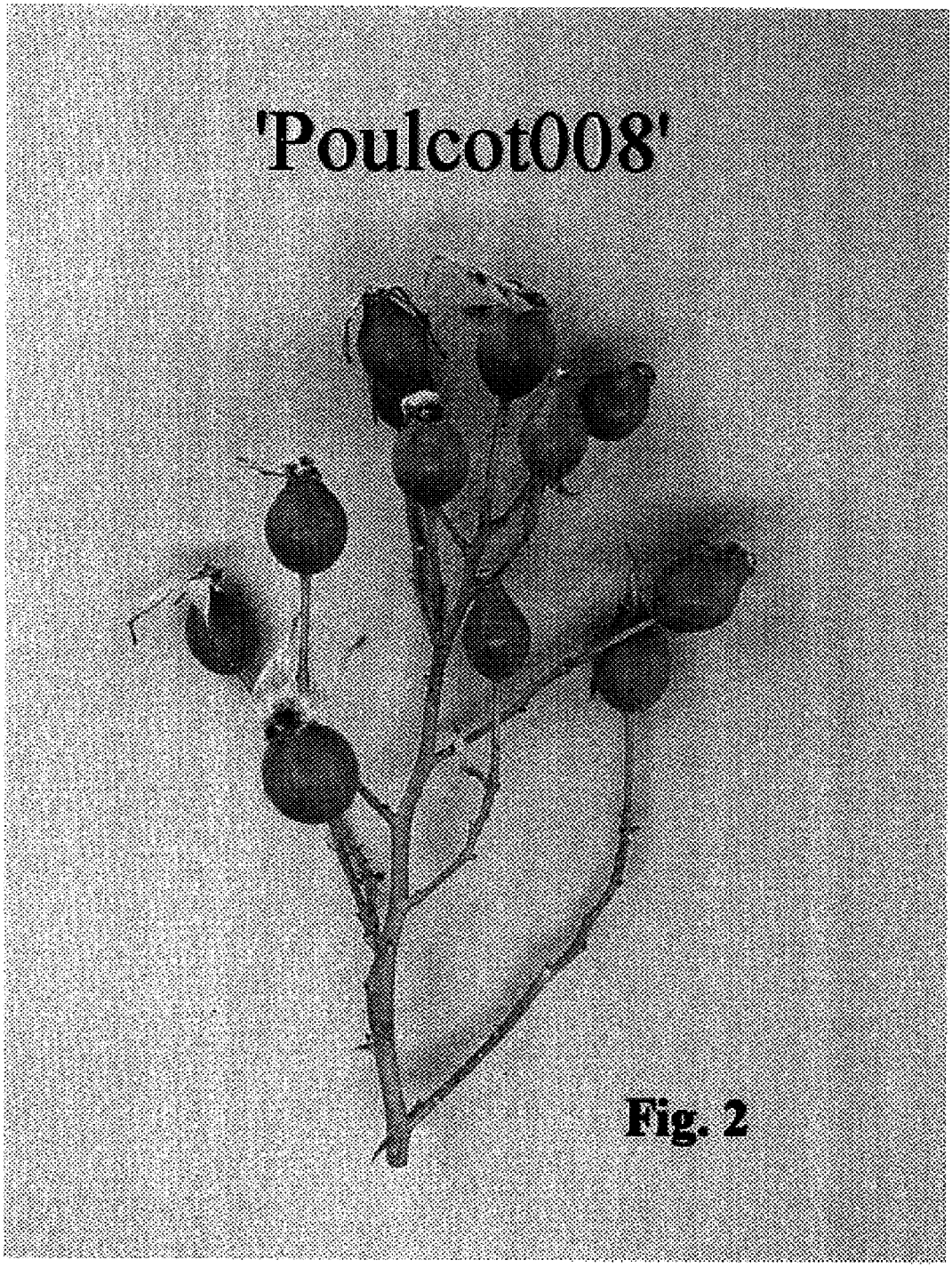
FIG. 2; Rose hips.

The following is a description of 'Poulcot008', as observed in its growth in a field nursery in Jackson County, Oreg. Observed plants are 2 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulterp', a rose variety from the same inventors described and illustrated in U.S. Plant Pat. No. 12,623 issued May 14, 2002, are compared to 'Poulcot008' in chart 1.

CHART 1

| | 'Poulcot008' | 'Poulterp' |
|---|---|---|
| General tonality. | White Group 155D. | White Group 155C. |
| Flower bud color when sepals first unfold. | Red Group 38C to White Group 155A. | White Group 155D. |
| Flower bud length. | 20 mm. | 15 mm. |

FLOWER AND FLOWER BUD

Blooming habit: Continuous.

Flower bud:

*Size.*—Upon opening, 20 mm in length from base of receptacle to end of bud. Bud diameter is 8 mm.

*Bud form.*—Ovate.

*Bud color.*—As sepals unfold, petals are Red Group 38C to White Group 155A.

*Sepal inner surface.*—Color: Green Group 138C. Surface: Weak pubescence observed.

*Sepal outer surface.*—Color: Yellow-Green Group 144A. Anthocyanic pigments Greyed-Red 183B. Texture: Smooth.

*Sepal shape.*—Apex: Cirrhose. Base: Flat at union with receptacle.

*Sepal margin.*—Margins have medium foliaceous appendages on three of the five sepals. Stipitate glands sparsely present.

*Sepal size.*—20 mm (l)×5 mm (w).

*Receptacle.*—Texture: Smooth. Shape: Elliptical. Size: 7 mm (h)×3.5 mm (w). Color: Yellow-Green Group 144A. Anthocyanic pigments the color of Greyed-Red Group 178A.

*Peduncle.*—Length: Variable. 24 cm at the lower portion of the flower cluster to 7 cm at the upper portion of the flower cluster. Diameter: 2 mm on average. Color: Yellow-Green Group 144B. Anthocyanic pigments Greyed-Red Group 182A.

*Pedicel.*—Surface: Smooth. Length: 13 to 18 mm on average. Diameter: 2 mm on average. Color: Yellow-Green Group 146C. Anthocyanic pigments Greyed-Orange Group 177A. Strength: Weak.

Flower bud development: Flower buds are borne in clusters of 5 to 9 flower buds. Inflorescence type is a thyrse.

Flower bloom:

*Fragrance.*—None.

*Duration.*—The blooms have a duration on the plant of approximately 5 to 8 days. Petals fall cleanly away from plant after flowers have fully matured.

*Size.*—Flower diameter is 50 mm when open. Flower depth is 17 mm.

*Flower shape.*—Petals arranged in an almost flat position when fully open.

*Petalge.*—Under normal conditions, flowers have 11 petals total, 3 of which are petaloids.

*Petal color.*—Upon opening: Upper surface: White Group 155D with very faint intonations of Red Group 56C. Lower surface: White Group 155D with very faint intonations of Red Group 56D. Basal petal spots, upon opening: No distinctive coloration at the petal base observed. After opening: Upper surface: White Group 155D with very faint intonations of Red Group 56C. Lower surface: White Group 155D with very faint intonations of Red Group 56D. Basal petal spots, upon opening: No distinctive coloration at the petal base observed.

General tonality: On open flower White Group 155D. No change in tonality.

Petals:

*Petal reflex.*—Flat.

*Margin.*—Entire with point at the center.

*Shape.*—Generally narrow elliptical. Apex: Cuspidate. Base: Acute.

*Size.*—23 mm (l)×19 mm (w).

*Texture.*—Smooth.

*Thickness.*—Thin.

*Arrangement.*—Not formal.

Petaloids:

*Quantity.*—3.

*Size.*—4 mm (l)×4 mm (w).

*Shape.*—Irregular, somewhat broad elliptical.

*Color.*—White Group 155D with very faint intonations of Red Group 56C.

Reproductive organs:

*Pollen.*—None observed.

*Anthers.*—Size: 2 mm in length. Color: Yellow-Orange Group 20A. Quantity: 60 on average.

*Filaments.*—Color: Yellow-White Group 158D. Length: 4 to 5 mm.

*Pistils.*—Length: 3 to 4 mm. Quantity: 15 on average.

*Stigmas.*—Superior in location relative to the length of the filaments and the height of the anthers. Color: Yellow-Green Group 145D.

*Styles.*—Color: Yellow-Green Group 145D.

*Hips.*—Color: Greyed-Orange Group 171A. Size: 12 mm (l)×14 mm (w).

*Seed.*—Quantity: 20 on average. Size: 5 mm (l)×3 mm (w). Color: Greyed-Yellow Group 160B.

PLANT

Plant growth: Bushy, spreading and low growing. When grown as a budded field grown plant on *Rosa multiflora* understock, the average height of the plant is 40 cm and the average width is 40 cm.

Stems:

*Color.*—Juvenile growth: Yellow-Green Group 144B. Anthocyanic intonations of Greyed-Orange Group 174A. Mature growth: Yellow-Green Group 146C.

*Length.*—On average, canes are 35 to 50 cm from the base of the plant to the flowering portion.

*Diameter.*—5 mm.

*Internodes.*—On mature canes, there is an average distance of 16 mm between nodes.

*Surface texture.*—Young wood: Smooth. Older wood: Smooth.

Thorns:

*Incidence.*—17 thorns per 10 cm of stem on average.

*Size.*—7 mm.

*Shape.*—Upper side: Concave to flat. Lower side: Deeply concave.

*Color.*—Juvenile thorns: Greyed-Red Group 181A. Mature thorns: Greyed-Yellow Group 161A.

Plant foliage: Normal number of leaflets leaves in middle of the stem: 7 leaflets.

*Compound leaf.*—77 mm (l)×47 mm (w).

*Quantity.*—4 to 5 leaves per 10 cm of stem on average.

*Color of mature foliage.*—Upper side: Yellow-Green Group 147A. Lower side: Yellow-Green Group 147B.

*Color of juvenile foliage.*—Upper side: Yellow-Green Group 146B. Anthocyanic intonations Greyed-Red Group 180A on the margins. Lower side: Yellow Green Group 146B.

Plant leaves and leaflets:

*Stipules.*—Size: 20 mm in length. Shape: Linear, slightly broad based with outward extending apecies. Margins: Finely serrated with many stipitate glands. Color: Yellow-Green Group 146A to 147A.

*Petiole.*—Length: 20 mm. Diameter: 2 mm.

*Upper surface.*—Color: Yellow-Green Group 146A. Observations: Few stipitate glands at margins.

*Lower surface.*—Color: Yellow-Green Group 146C. Observations: Smooth.

*Rachis.*—Length: 25 to 30 mm average. Upper surface: Color: Yellow-Green Group 146A. Observations: Few stipitate glands at margins. Lower surface: Color: Yellow-Green Group 146C. Observations: Smooth.

*Leaflet.*—Edge: Serrated. Size: Average size of the terminal leaflet on normal leaves is 20 mm (l)×10 mm (w). Shape: Ovate. Base: Obtuse. Apex: Acuminate. Texture: Smooth. Thickness: Average. Arrangement: Odd pinnate. Venation: Reticulate. Glossiness: Glossy.

Disease resistance: Above average resistance to powdery and downy mildews, rust, black spot, and *Botrytis* under normal growing conditions in Jackson County, Oreg.

Cold hardiness: The variety 'Poulcot008' has been found to be cold tolerant to USDA Cold Hardiness Zone 6.

I claim:

1. A new and distinct variety of rose plant of the shrub rose class named 'Poulcot008', substantially as illustrated and described herein as a distinct variety and novel rose variety due to its abundant white flowers, disease resistance, abundant rose hips, and extended period of bloom.

* * * * *

'Poulcot008'
Fig. 1.1
Fig. 1.2
Fig. 1.3
Fig. 1.4
Fig. 1.5
Fig. 1.6